(12) United States Patent
Mayr

(10) Patent No.: US 7,976,482 B2
(45) Date of Patent: Jul. 12, 2011

(54) DEVICE AND METHOD FOR KNEE LIGAMENT STRAIN MEASUREMENT

(76) Inventor: Hermann Mayr, Grosshesselohe (DE)

( * ) Notice: Subject to any disclaimer, the term of this patent is extended or adjusted under 35 U.S.C. 154(b) by 0 days.

(21) Appl. No.: 12/393,777

(22) Filed: Feb. 26, 2009

(65) Prior Publication Data

US 2009/0264797 A1    Oct. 22, 2009

(30) Foreign Application Priority Data

Apr. 16, 2008   (EP) ..................................... 08154617

(51) Int. Cl.
*A61B 5/117*   (2006.01)
*A61B 5/103*   (2006.01)

(52) U.S. Cl. ........................................ 600/595; 600/592
(58) Field of Classification Search .................. 600/587, 600/595, 592; 482/79, 80
See application file for complete search history.

(56) References Cited

U.S. PATENT DOCUMENTS

| | | |
|---|---|---|
| 4,583,555 A | 4/1986 | Malcom et al. |
| 4,733,859 A | 3/1988 | Kock et al. |
| 4,913,163 A | 4/1990 | Roger et al. |
| 5,957,869 A | 9/1999 | Caruso et al. |
| 2009/0124936 A1* | 5/2009 | Branch et al. ................. 600/587 |

FOREIGN PATENT DOCUMENTS

| | | |
|---|---|---|
| EP | 0 496 528 | 7/1992 |
| EP | 0 568 148 | 11/1993 |
| EP | 1 364 636 | 11/2003 |
| WO | WO 87/05789 | 10/1987 |
| WO | WO 93/02621 | 2/1993 |
| WO | WO 2005/104945 | 11/2005 |

* cited by examiner

*Primary Examiner* — Max Hindenburg
*Assistant Examiner* — Brian Szmal
(74) *Attorney, Agent, or Firm* — Dickstein Shapiro LLP

(57) ABSTRACT

A device for measuring displacement of the tibia in relation to the femur in response to an applied force or torque on the tibia. A first shaft is tiltable about a first axis close to the ankle and approximately parallel to the coronal plane of the patient's body. A second shaft is connected to the first shaft and is rotatable about a second axis perpendicular to the first axis, and is close to the ankle and approximately parallel to the tibia. A foot support platform is mounted on the second shaft, the foot support platform being configured for attachment of the foot at a fixed position. A displacement test device is provided for applying forces to the tibia and measuring the shift or displacement of the proximal tibia relative to the distal femur.

15 Claims, 4 Drawing Sheets

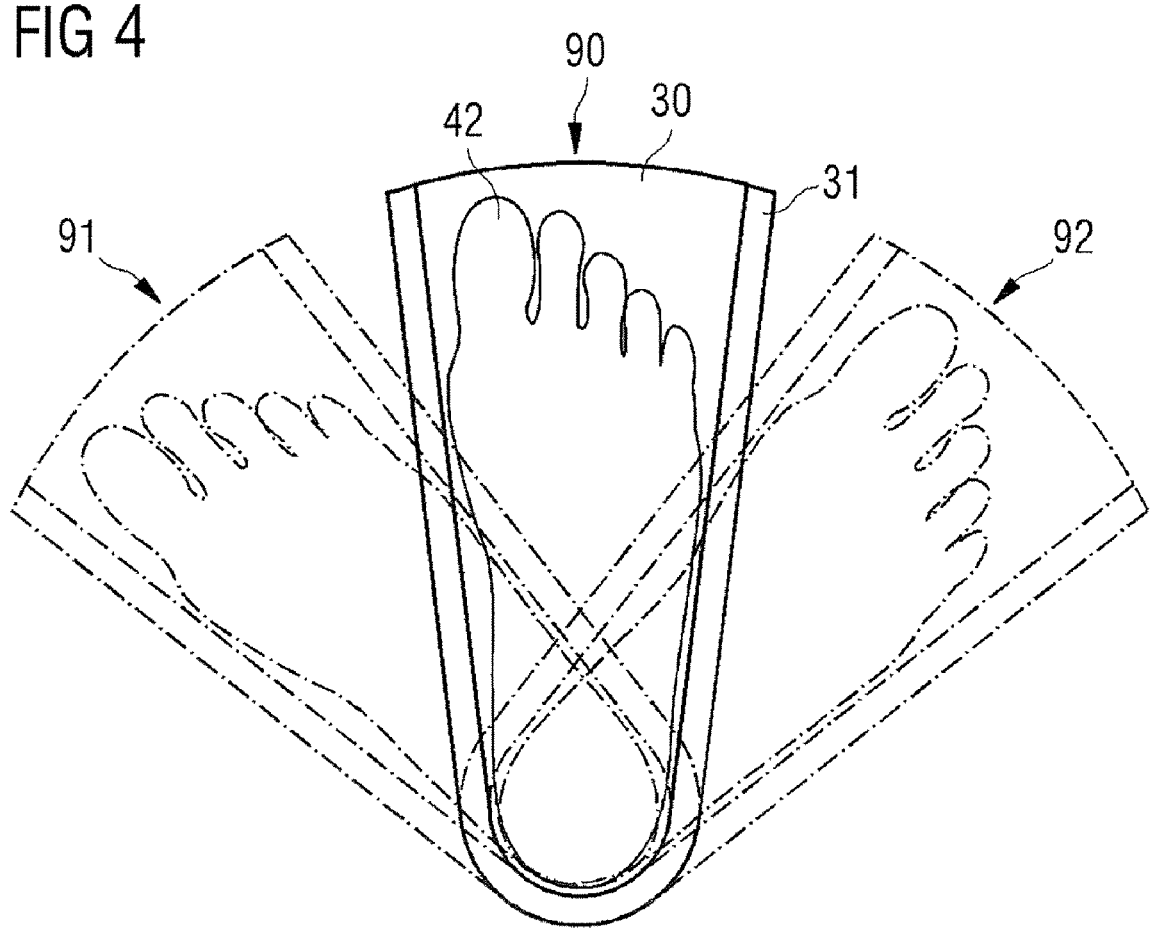

DEVICE AND METHOD FOR KNEE LIGAMENT STRAIN MEASUREMENT

FIELD OF THE INVENTION

The invention relates to a medical device and a method for measuring displacement of the proximal tibia relative to the distal femur as a result of applied forces.

DESCRIPTION OF THE PRIOR ART

When exercising sports, damage to the anterior and/or posterior cruciate ligament and the capsule of the knee is a common consequence of trauma of the knee. Various methods are known for analyzing the status of the knee. A manual test which can be performed by an orthopedic surgeon is the Lachman test. The results are rather unreproducible owing to varying positions and varying force applied to the knee. Especially if performed by different persons, for example for comparing the pre- and postoperative status, the results are hardly comparable.

In the U.S. Pat. No. 4,583,555 a device for controlled measurement is disclosed. With this device the surgeon can apply a predetermined force to the tibia and measure the displacement between the femur and the tibia. This device does still not allow analysis of knee stability in internal and external rotation of the lower leg. Furthermore, it is susceptible to slightly varying positions of the patient, specifically because the tibia is not exactly fixed.

Another device for measuring the drawer shift is disclosed in U.S. Pat. No. 4,913,163. This device provides an ankle support for holding the patient's ankle by straps surrounding the ankle. This device suffers from the same problem as the device mentioned previously.

SUMMARY OF THE INVENTION

It is a general object of the present invention to provide a system and a method for testing the condition of knee ligaments that provides an objective measurement of displacement between the proximate tibia and the distal femur with higher repeatability and precision.

The invention comprises a foot support platform 13 which can be tilted about at least two axes. The first axis is close to the ankle 43 and approximately parallel to the coronal plane of a patient's body. Tilting about this axis results in dorsiflexion of the foot 42, increasing the dorsiflexion angle of the ankle (neutral zero method). The second axis is at right angle to the first axis and again approximately at the ankle 43, but approximately parallel to the tibia 46, thus permitting the foot 42 to perform internal and external rotation. The second axis may also deviate from the axis of the tibia by a predetermined angle or the angle from the tilt on the first axis. Furthermore, an optional thigh support platform 51 is provided to support the thigh 40 and bring the knee 44 into a predetermined angle, preferably in the range of 10 to 40 degrees, most preferably 30 degrees or 90 degrees.

Before performing a measurement with the displacement test device 60, the patient is placed with his knee 44 on the thigh support platform 51 and the foot 42 is placed on the foot support platform 30. The foot 42 is fixed on the platform 30 either with straps 32 or with a fixation frame 31 or by any other adequate means or a combination thereof. Such a fixation allows precise rotation. Preferably the foot is fixed within the foot support platform by the posterior area of the heel and the metatarsal head 1 and 5. Preferably the frame 31 is adjustable to fit exactly to the width of the foot between metatarsal heads 1 and 5. Such adjustment may be performed by adjustment screws 33 movable in slots.

In a first step, the foot support platform 30 is placed into an upright position close to the natural position of the foot. In a next step, the foot support platform is tilted around the first axis by the first shaft 10, so that the forefoot moves into dorsiflexion. Tilting should be done in such a way that maximum dorsiflexion is obtained. This tilt is either performed at a constant angle or at a constant force. Preferably, a constant force is applied and the resulting angle is measured. Preferably the force is adjusted to obtain maximum dorsiflexion. By this flexion the upper ankle is locked in rotation.

The value of the constant force may be a predetermined value, preferable in a range of 2 N to 15 N. It is further preferred to apply a predetermined torque instead of a predetermined force. The torque may be directly applied to the first shaft by means of a drive motor or by a torque wrench. The torque may be any predetermined value, preferable in a range of 1 Nm to 15 Nm. Most preferably the range is between 1 Nm to 10 Nm.

After the upper ankle is locked against rotation, the foot 42 is rotated into predetermined positions by rotating the second shaft 20. This can be done either by applying a predetermined rotational angle or by applying a predetermined force or torque to rotate the foot against the left and right end positions. Doing so imposes a torque on the knee 44 because the tibia 46 cannot rotate relative to the foot 42 as it has been locked in the previous flexion on the first shaft 10. Preferably the inventive device is used for measuring the necessary force or torque for obtaining a rotation through a predetermined angle, or measuring the rotated angle after applying a predetermined force or torque to rotate the foot. The respective measurement devices for measuring force, torque or angle are optionally provided.

In another embodiment of the invention a displacement test device 60 is provided. This displacement test device applies a predetermined force or torque to the tibia and measures displacement of the proximal tibia 46 relative to the distal femur 56. Such a force may be applied in any direction, preferably at right angles to the tibia. This measurement is also referred to as anterior posterior translation measurement. Such a measurement can be repeated with various displacement angles of the foot 42 around the second shaft.

In a further embodiment of the invention, a displacement test device 60 is provided as disclosed in U.S. Pat. No. 4,583,555 for specifically performing a drawer shift measurement. This document is included herein by reference. It applies a predetermined force to the tibia and permits measurement of the displacement between the proximate tibia and the distal femur.

In another embodiment of the invention, at least one side stop 65 is provided for applying varus—valgus stress on the medial or lateral epicondyle of the distal femur. Such a side stop may be manually or automatically driven or positioned to fix the distal femur at a predetermined position. Alternatively, the side stops may impose a predetermined force on either side of the distal femur. Drive means may be provided to move the side stops.

It is obvious that instead of the described first and second shafts, hinges or other means for allowing a tilt of the foot support platform also may be used.

Furthermore, the first and second shafts may be driven by a DC motor, a stepper motor or a torque wrench. optionally such a drive means has means for stopping tilt and/or rotation motion after a predetermined position and/or a predetermined force has been reached.

In general the various embodiments described in this document may be combined with each other.

A method for measuring the anterior or posterior displacement of the proximal tibia 46 relative to the distal femur 56 as a result of applied forces comprises the following steps:

Flexing the foot 42 of a patient around a first axis for dorsiflexion. This first axis propagates through a point close to the ankle 43 and approximately parallel to the coronal plane of the patient body. Flexing is either done by applying a predetermined torque towards the patient's body or by performing flexion until at least one of a predetermined angle, a predetermined torque or a predetermined force has been reached. This results in locking the foot 42 against the tibia 46.

Rotating the foot 42 about a second axis, which is approximately parallel to the tibia axis 48, either to the left or to the right of the patient by applying a constant torque or by rotating until at least one of a predetermined angle, a predetermined torque or a predetermined force has been reached.

Performing a displacement measurement, preferably by applying a force or a torque to the tibia 46 and measuring the displacement of the proximal tibia 46 relative to the distal femur 56.

Equivalent to the first step of flexing around a first axis, is a shifting of the top section of the foot 42 close to the toes towards the body of the patient. This shift may be done by applying a predetermined force or by shifting for a predetermined distance or by shifting until a predetermined force has been reached.

Rotating in the second step may also be performed by a shift operation of the foot to the left side or to the right side of the patient. This may be done by applying a constant force or by either shifting until a predetermined distance or a predetermined force has been reached. This shift will result in a rotation on the second axis as described above, as the ankle should be at a fixed position during the whole process.

To increase stability and reproducibility, preferably the foot 42 is fixed onto a foot support platform 30, preferably by a side frame 31 and/or by straps 32 like Velcro straps. Preferably fixing the foot 42 on the foot support platform 30 is done with a natural position of the foot. Furthermore, it is preferred that the knee 44 is held in a predetermined position, specifically resulting in a predetermined angle between the femur axis 47 and the tibia axis 48. This can be done by a thigh support platform 51 which is placed under the knee 44 of the patient lying on the examining table 50. Further stabilization of the knee may be performed by additional side stops 65 which may be pressed by a predetermined force against the knee to either the medial or the lateral side or both sides. The force is preferably in a range between 1 N and 15 N.

To reach maximum dorsiflexion in the first flexing step, the following steps may be executed once or repeated instead of a single flexion according to the first flexing step:

flexing the foot towards the patient for dorsiflexion with a constant torque, at a predetermined first force or until a predetermined first position or a predetermined first force has been reached, flexing into the opposite position for a predetermined time or a predetermined position, flexing towards the patient for dorsiflexion with a constant torque, at a predetermined second force or until a predetermined second position or a predetermined second force has been reached.

Furthermore, in the second rotation step rotating may be replaced by the following steps which optionally may be repeated:

rotating the foot in a first direction with a predetermined first torque, at a predetermined first force or until a predetermined first position or a predetermined first force has been reached, rotating in the opposite direction for a predetermined time or into a predetermined position, rotating in the first direction with a predetermined second torque, at a predetermined second force, or until a predetermined second position or a predetermined second force has been reached.

Preferably the predetermined second torque or the predetermined second force is equal or it is higher than the predetermined first torque or the predetermined first force.

Optionally the measurement step may be supplemented by:

rotating the foot support platform into the opposite direction, applying at least one force to the tibia in relation to the femur or the patella, measuring displacement between the tibia and the femur or the patella.

These steps also may be repeated several times.

BRIEF DESCRIPTION OF THE DRAWINGS

In the following the invention is described by way of example without limitation of the general inventive concept with the aid of embodiments and with reference to the drawings to which attention is expressly drawn concerning a disclosure of details of the invention not described more explicitly in the text.

FIG. 4 is a plantar view of the foot and the foot support platform.

DETAILED DESCRIPTION OF THE PREFERRED EMBODIMENTS

Figure 1:
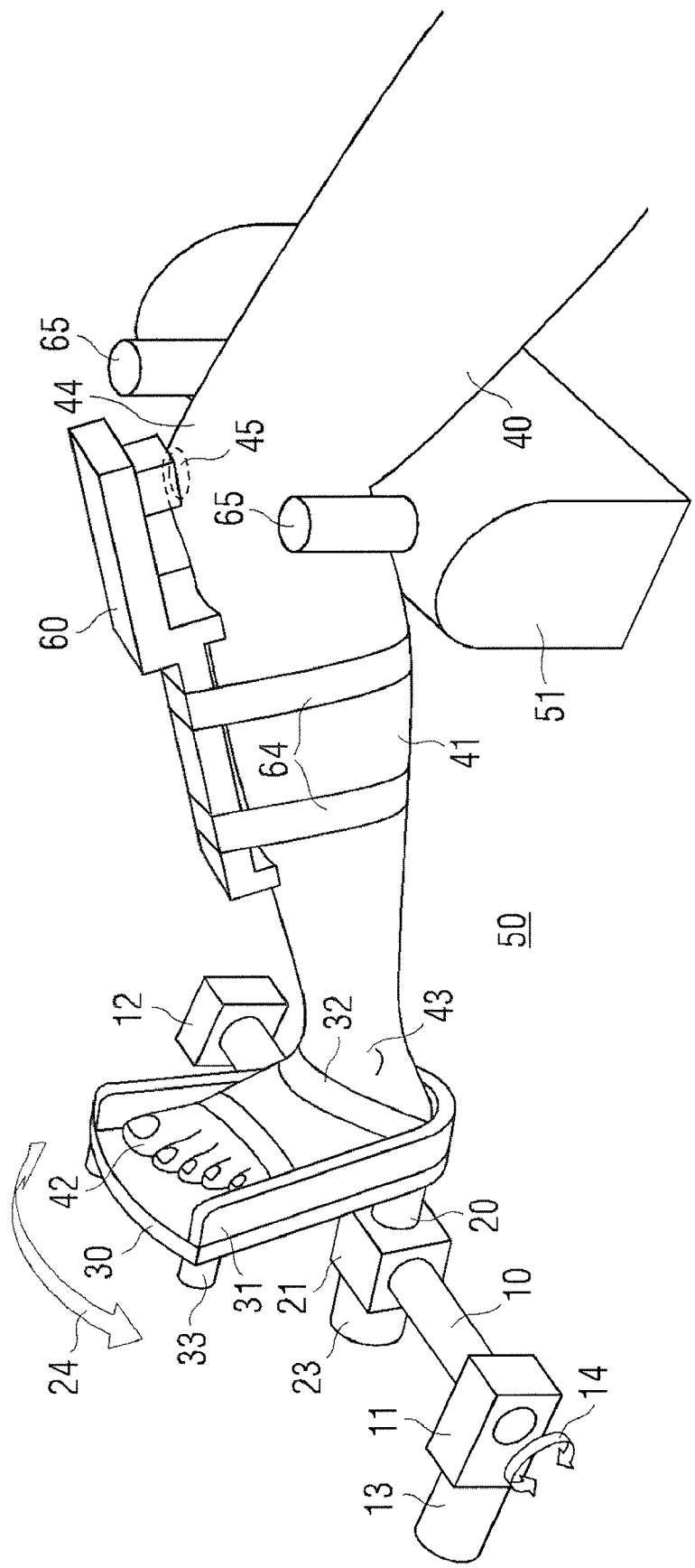
FIG. 1 is a perspective view of the device operatively attached to the leg of a patient.

Referring to FIG. 1, the lower leg of the patient lying on the examining table 50 is shown. It comprises thigh 40, shank 41 and ankle 43. The knee 44 is supported by a thigh support platform 51. The foot 42 is positioned into a foot support platform 30 and fixed therein by a frame 31 which may be adjusted to the size of the foot by adjustment means 33. In addition, straps like Velcro straps 32 may be used to secure the foot on the foot support platform. Furthermore, additional straps 64 like Velcro straps may be used to secure the knee against the thigh support platform 51. Furthermore, the thigh support platform may have additional side stops 65 to prevent lateral movement of the knee.

The foot support platform 30 is mounted tiltable about at least two axes relative to the examining table 50. A tilt movement 14 of the foot support platform 30 around the first axis can be performed by rotation of a first shaft 10. This first shaft 10 is held by means of the bearings 11 and 12 against the examining table or an intermediate platform which may hold the whole device. To ensure a reproducible tilt of the foot support platform, drive means 13 are provided. These drive means may be either a drive motor like an electrical motor, preferable a DC motor or a stepper motor. Alternatively, this may be a standard adapter for a torque wrench. Of course any other means for achieving angular movement of the first shaft 10 is acceptable. This may also be achieved by a linear displacement device like a hydraulic or pneumatic cylinder together with a lever.

For rotating 24 the foot support platform around the second axis, being approximately parallel to the axis of the tibia, a second shaft 20 is provided. This second shaft 20 is supported by means of one or several bearings 21 against the first shaft and is tiltable together with the first shaft around the axis of the first shaft. Furthermore, drive means 23 are provided for driving the second shaft. These drive means may be similar to the drive means described previously for the first shaft.

For performing the displacement measurement, a displacement test device 60 is provided. It is attached to the shank 41 by means of straps and measures the drawer shift related to the patella 45.

Figure 2:
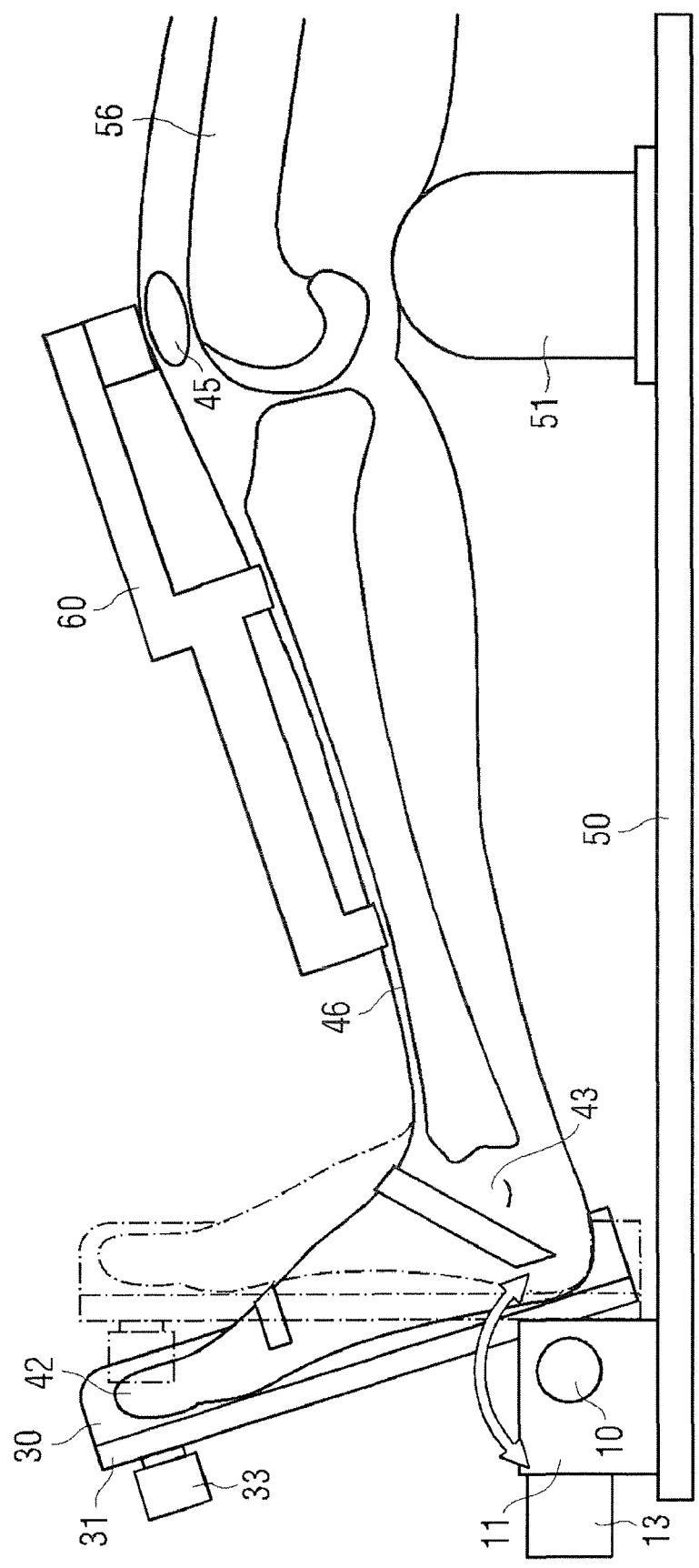
FIG. 2 shows a cross-section of the lower leg of the patient together with the device.

FIG. 2 shows a cross-section of the lower leg of the patient with the inventive device. Herein the tibia 46, femur 56 and patella 45 are shown in more detail. Furthermore the foot 42 is shown in the natural position and in the flexed position (dashed lines).

Figure 3:
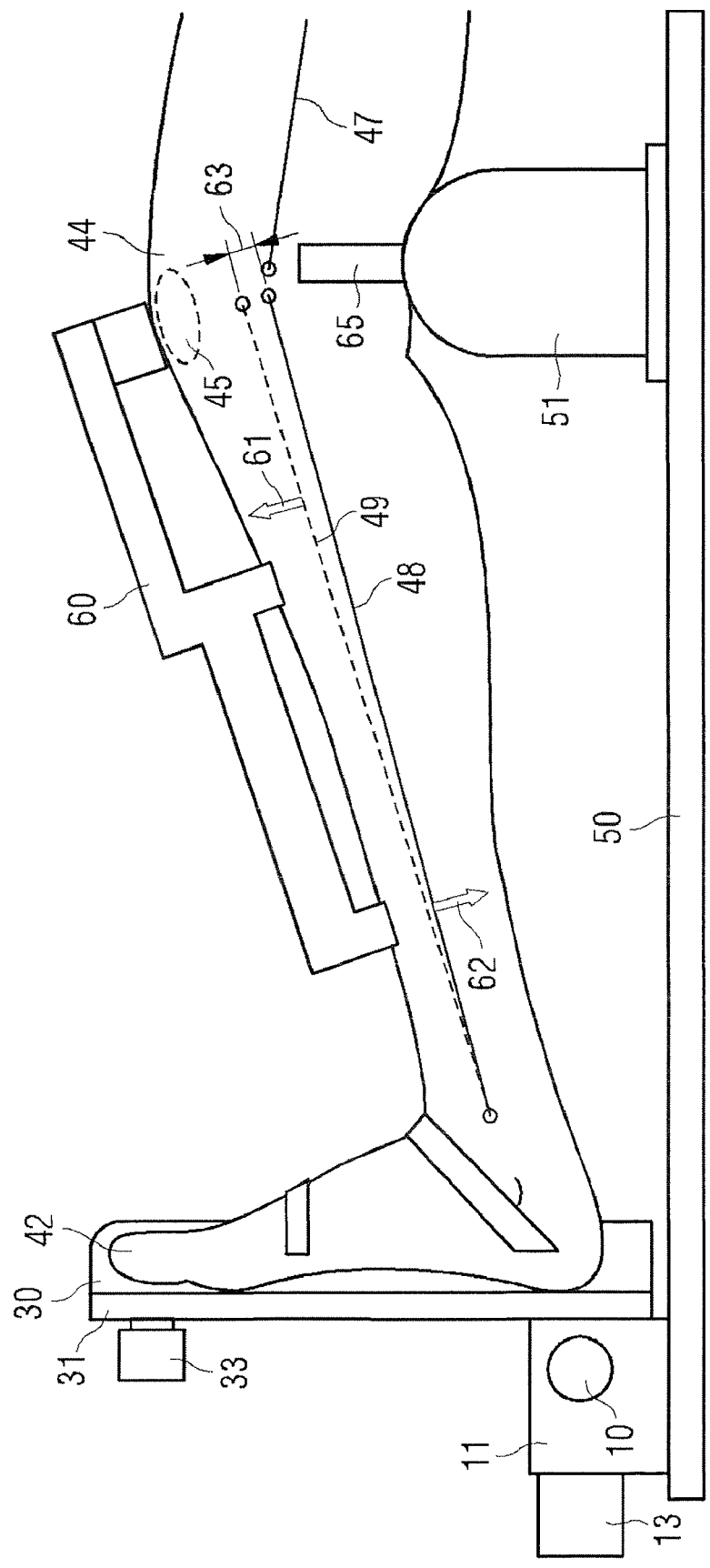
FIG. 3 shows geometrical characteristics of the inventive device.

In FIG. 3, the geometrical characteristics of the invention are shown. When placing the patient's leg on the examining table, the femur axis 47 is positioned against the tibia axis 48 by a predetermined angle. Flexion of the foot is performed about a first axis by means of the first shaft 10 and rotation about the foot is performed by means of the second shaft 20.

Operation of the displacement test device is described by partially referring to FIGS. 1 and 2. The displacement test device 60 asserts a force against the tibia 46 in relation to the femur 56. This force may be in any direction, preferably at right angles to the tibia. Dependent on the integrity of the anterior and posterior cruciate ligaments of the knee, applying of the displacement force results in a shift between the tibia 46 and the femur 56. While the foot is secured by means of the foot support platform 30, preventing the foot from moving, asserting this force 61 results in a torque on the tibia around an axis at the ankle 43. Similarly, a torque can also be asserted by applying a second force 62 at a location different from the location where the first force 61 is applied. This also results in a torque on the tibia 46. At a position of the knee between the femur and the tibia, the torque results in a displacement force shifting the tibia and accordingly the tibia axis 48 into a displaced position 49. The displacement 63 can be measured by the displacement test device 60.

In a specific embodiment a drawer shift measurement is performed. Here a force 62 is applied in an upward direction, preferably at right angle to the tibia axis.

In a further embodiment of the invention, shift measurement is done as disclosed in the U.S. Pat. No. 4,583,555 by referring to the patella 45 instead of the femur 55, as the patella is comparatively stiff attached to the femur. Accordingly, using the patella for applying force and/or for measuring the shift is advantageous.

This shift may be in a range from 2 mm up to more than 20 mm with damaged cruciate ligaments. The measurement and the evaluation of the displacement can be made manually, semi-automatically, or fully automatically. In addition, a plotter may be attached to the displacement test device to draw a plot of the force against displacement. This may also be recorded by a computer or by any other device like a data recorder.

FIG. 4 shows a view from bottom of the foot 42 towards the patient. A rotation about the second axis, approximately parallel to the tibia axis, is shown. From the natural position 90 the foot is either turned to the right, resulting in an outwards position 92 for the shown left foot, or turned to the left, resulting in an inwards position 91.

What is claimed is:

1. A device for measuring displacement of the tibia (46) in relation to the femur (56) in response to an applied force or torque on the tibia and/or the femur, comprising
    a first shaft (10) being tiltable about a first axis close to the ankle and parallel to the coronal plane of a patient's body,
    a second shaft (20) being connected to said first shaft (10) and being rotatable about a second axis perpendicular to said first axis, being close to the ankle and parallel to the tibia,
    a foot support platform (30) being mounted on said second shaft (20), the foot support platform having means for attaching the foot thereto at a fixed position,
    at least one displacement test device (60) for applying forces to the tibia and either measuring displacement of the proximal tibia (46) relative to the distal femur (56) or measuring drawer shift, and
    either at least one means (13, 23) for driving at least one of said first shaft (10) or second shaft (20) with a predetermined torque and/or with a predetermined force or at least one means (13, 23) for driving at least one of said first shaft (10) or second shaft (20), and means for stopping tilt or rotation motion after a predetermined position and/or predetermined force has been reached.

2. Device according to claim 1, further comprising at least one side stop (65) for applying varus—valgus stress on the medial or lateral epicondyle of the distal femur.

3. Device according to claim 1, wherein at least one means (13, 23) for driving at least one of said first shaft (10) or second shaft (20) is a DC motor, a stepper motor, or a torque wrench.

4. Device according to claim 1, further comprising a thigh support platform (51) for supporting the lower leg and positioning the axis of the femur (47) and the axis of the tibia (48) at a predetermined angle.

5. Device according to claim 1, wherein the foot support platform (30) has means (32) for affixing the foot at a predetermined position.

6. Device according to claim 1, wherein the foot support platform (30) has a frame (31) surrounding at least parts of the foot and the frame (31) is adjustable to the size of the foot.

7. Method for measuring displacement of the tibia (46) with respect to the femur (56) in response to an applied force on the tibia, comprising the steps of:
    a) affixing the foot (42) to a foot support platform (30), the foot platform being positioned close to a natural position of the foot,
    b) tilting the foot support platform (30) about a first axis close to an ankle and parallel to the coronal plane of the patient's body for dorsiflexion, the first axis is defined by a first shaft which is connected to a second shaft which defines a second axis,
    c) rotating the foot support platform (30) about the second axis which is perpendicular to the first axis, and
    d) measuring the rotational angle at a predetermined force or torque or measuring the force or torque at a predetermined rotational angle.

8. Method according to claim 7, wherein the foot support platform (30) is tiltable for maximum dorsiflexion about the first axis.

9. Method for measuring displacement of the tibia (46) with respect to the femur (56) in response to an applied force on the tibia, comprising the steps of:
   a) affixing the foot (42) to a foot support platform (30), the foot platform being positioned close to a natural position of the foot,
   b) tilting the foot support platform (30) about a first axis close to the ankle and parallel to the coronal plane of the patient's body for dorsiflexion, the first axis is defined by a first shaft which is connected to a second shaft which defines a second axis,
   c) rotating the foot support platform (30) about the second axis which is perpendicular to the first axis in a first direction,
   d) applying at least one force to the tibia in relation to the femur or the patella, and
   e) measuring displacement between the tibia and the femur or the patella.

10. Method according to claim 9, wherein the tilting in step b) is performed by a predetermined force or that tilting in step b) is finished when at least one of a predetermined angle, a predetermined position, or a predetermined force has been reached.

11. Method according to claim 9, wherein the tilting in step b) comprises the following steps:
   b1) tilting the foot towards the patient for dorsiflexion with a constant torque, at a predetermined first force, or until a predetermined first position or a predetermined first force has been reached,
   b2) tilting into the opposite position for a predetermined time or a predetermined position,
   b3) tilting towards the patient for dorsiflexion with a constant torque, at a predetermined second force or until a predetermined second position or a predetermined second force has been reached,
   b4) optionally repeating previous tilting steps b1) to b3).

12. Method according to claim 9, wherein the tilting in step c) comprises the following steps:
   c1) rotating the foot in said first direction with a predetermined first torque, at a predetermined first force, or until a predetermined first position or a predetermined first force has been reached,
   c2) rotating in the opposite direction for a predetermined time or a predetermined position,
   c3) rotating in the first direction at a predetermined second torque, with a predetermined second force or until a predetermined second position or a predetermined second force has been reached,
   c4) optionally repeating previous tilting steps c1) to c3).

13. Method according to claim 9, further comprising the steps of:
   f) rotating the foot support platform in an opposite direction to step c),
   g) applying at least one force to the tibia in relation to the femur or the patella,
   h) measuring the displacement between the tibia and the femur or the patella.

14. Method according to claim 9, further comprising repeating all steps and performing multiple measurements for reducing reading errors.

15. Method according to claim 9, wherein the foot support platform (30) is tiltable for maximum dorsiflexion about the first axis.

\* \* \* \* \*